(12) United States Patent
Messinger et al.

(10) Patent No.: US 8,016,336 B2
(45) Date of Patent: Sep. 13, 2011

(54) MOBILE RADIATION THERAPY

(76) Inventors: Samuel Messinger, Miami Beach, FL (US); Mark Elliot Pomper, Miami Beach, FL (US)

( * ) Notice: Subject to any disclaimer, the term of this patent is extended or adjusted under 35 U.S.C. 154(b) by 23 days.

(21) Appl. No.: 12/189,514

(22) Filed: Aug. 11, 2008
(Under 37 CFR 1.47)

(65) Prior Publication Data
US 2009/0175414 A1 Jul. 9, 2009

Related U.S. Application Data

(63) Continuation of application No. 11/936,189, filed on Nov. 7, 2007, now abandoned.

(51) Int. Cl.
*A61G 3/00* (2006.01)
(52) U.S. Cl. ...................................... 296/24.38
(58) Field of Classification Search ............... 296/24.38, 296/24.3, 19; 5/601; 250/505.1, 506.1, 515.1, 250/517.1, 493.1
See application file for complete search history.

(56) References Cited

U.S. PATENT DOCUMENTS

| | | | | |
|---|---|---|---|---|
| 4,181,347 A | * | 1/1980 | Clark | 378/199 |
| 4,449,746 A | * | 5/1984 | Clark | 378/208 |
| 4,833,335 A | * | 5/1989 | McGinley et al. | 250/518.1 |
| 5,048,070 A | * | 9/1991 | Maehama et al. | 378/197 |
| 5,727,353 A | * | 3/1998 | Getz et al. | 52/79.1 |
| 6,082,799 A | * | 7/2000 | Marek | 296/24.38 |
| 6,445,185 B1 | * | 9/2002 | Damadian et al. | 324/319 |
| 6,481,887 B1 | * | 11/2002 | Mirabella | 378/198 |
| 7,276,716 B1 | * | 10/2007 | Munro, III | 250/515.1 |
| 7,530,616 B2 | * | 5/2009 | Pomper | 296/24.38 |
| 7,733,089 B2 | * | 6/2010 | Hobbs et al. | 324/319 |
| 2007/0164238 A1 | * | 7/2007 | Pomper | 250/493.1 |
| 2009/0252293 A1 | * | 10/2009 | Pomper | 378/65 |
| 2009/0268870 A1 | * | 10/2009 | Pomper | 378/65 |

FOREIGN PATENT DOCUMENTS

WO WO-2004/075975 A2 * 9/2004

* cited by examiner

*Primary Examiner* — Jason S Morrow
(74) *Attorney, Agent, or Firm* — Greenberg Traurig LLP (57) ABSTRACT

A mobile radiation therapy apparatus includes a vehicle cabin including driving controls for the vehicle cabin. A patient treatment compartment is rigidly attached to the vehicle cabin. A high dose rate radiation source configured to emit radiation is disposed within the patient treatment compartment. A patient treatment table is disposed within the patient treatment compartment and in proximity to the radiation source. A radiation shield is disposed around the patient treatment table, the radiation shield including a plurality of radiation shield sections rigidly attached to the patient treatment compartment and configured to substantially impede the radiation emitted from the radiation source.

20 Claims, 6 Drawing Sheets

MOBILE RADIATION THERAPY

This application is a continuation of U.S. Non-Provisional application Ser. No. 11/936,189 filed Nov. 7, 2007 now abandoned, the entire disclosure of which is incorporated herein by reference.

BACKGROUND OF THE INVENTION

Radiation Therapy is one of the three primary methods to cure cancer, the others being surgery and chemotherapy. Radiation treatment typically requires multiple sessions (often over 20), and therefore may require a great deal of travel time wherein the patients must come into a cancer center for treatment. Additionally, patients are often required to endure prolonged time periods in waiting rooms at the cancer center for their treatments, even though these actual treatments are generally quick. This extensive queuing is most difficult for patients who are sick and infirm, which comprise a significant proportion of cancer patients.

This invention provides patients with a quality of radiation therapy which is substantially similar to current fixed location cancer centers, but without the need to travel to the center. The mobile aspects of the invention provide a quality treatment experience because fewer appointments are missed and a higher percentage of completed therapy protocols are accomplished. Additionally, a commonly seen phenomena of patient procrastination (i.e. wherein patients do not come to their initial consults, or even make their appointments) can be reduced. The invention assists in the treatment of patients who are currently unable (or are able only with major difficulties) to obtain radiation therapy.

Previous attempts to provide mobile radiation therapy are founded in the notion of merely creating satellite stationary treatment centers. For example, a radiation therapy center such as described in U.S. Pat. No. 4,449,746 can be set up in one location for an entire day, and then relocated to another location for the next day. Although this approach does create increased access to care, it fails to address the special needs of very sick and feeble patients because these patients must find the means to travel to the satellite center. The consequences of missing radiation therapy sessions or consultation visits can be life threatening.

OBJECTS AND SUMMARY OF THE INVENTION

It is therefore an object of the invention to provide an improved system and method for mobile radiation therapy. In one embodiment, a mobile radiation therapy apparatus includes a vehicle cabin including driving controls for the vehicle cabin. A patient treatment compartment is rigidly attached to the vehicle cabin. A high dose rate radiation source configured to emit radiation is disposed within the patient treatment compartment. A patient treatment table is disposed within the patient treatment compartment and in proximity to the radiation source.

A radiation shield is disposed around the patient treatment table, the radiation shield including a plurality of radiation shield sections rigidly attached to the patient treatment compartment and configured to substantially impede the radiation emitted from the radiation source.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION OF THE PREFERRED EMBODIMENT

Reference will now be made in detail to the preferred embodiments of the present invention, examples of which are illustrated in the accompanying drawings.

Embodiments of the invention provide techniques for diagnosing and evaluating medical conditions and providing appropriate treatment at a patient's home residence. A physician conducts an initial house call with a patient to gather personal and medical data. A mobile diagnostic x-ray team may be subsequently dispatched to the patient's home residence. A technical team reviews patient data to determine the proper therapy plan. Additional house visits and/or telephone interviews may be conducted. A mobile radiation therapy apparatus is dispatched to the patient's home as required by the therapy plan. The mobile radiation therapy apparatus includes a radiation source and shielding, and is capable of superficial radiation therapy and/or High Dose Rate (HDR) implant therapy. For HDR therapy, low dose particle therapy, protons, neutrons, ytterbium 169, low frequency vacuum tube (such as xoft, inc), cyber knife or any type of XRT therapy, the mobile radiation therapy apparatus itself is a specialized radiation vault which the patient will enter. Therapy data is stored in the mobile radiation therapy apparatus and transferred to the technical team for additional analysis. The technical team adjusts the therapy plan based on the additional analysis, and the mobile radiation therapy apparatus is dispatched in accordance with adjusted therapy plan.

Figure 1:
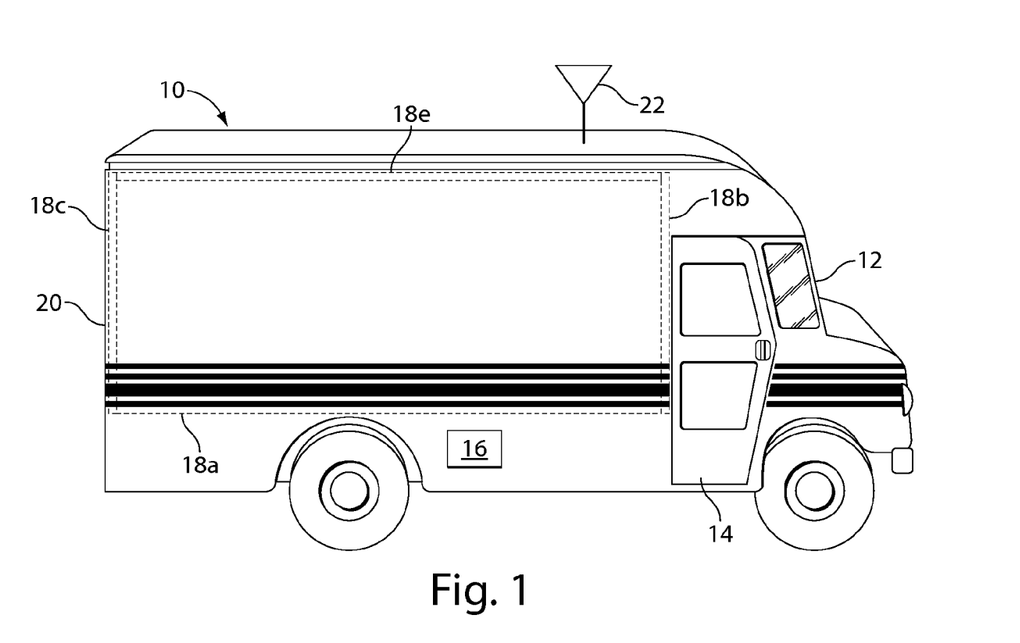
FIG. 1 is a profile, side view of a mobile radiation therapy apparatus.

Referring to FIG. 1, a mobile radiation therapy apparatus (MRTA) 10 comprises a vehicle cabin 12, at least one patient access door 14, an interface panel 16, radiation shielding sections 18a-e, a patient treatment compartment 20, and at least one wireless communication antenna 22. The MRTA 10, including the vehicle cabin 12 and the patient treatment compartment 20, is sufficiently compact in size to travel within an urban population center to a patient's parking lot or driveway (e.g. the patient treatment compartment is approximately 28' in length by 8' in width). The vehicle cabin 12 includes the driving controls for the MRTA 10 and is detachable from the patient treatment compartment 20. For example, the MRTA 10 is designed as a pod which is capable of being carried on a flatbed vehicle. In one embodiment, the MRTA 10 is designed as a trailer which is capable of being coupled and uncoupled from a vehicle. Further, the MRTA 10 is capable of being air-lifted into an area and operates independent of the vehicle (e.g., provide radiation therapy when roads have become inaccessible).

In one embodiment, such as for use in urban areas where street and parking space is generally less, the MRTA 10 includes a combination vehicle cabin 12 and patient treatment compartment 20 that are rigidly connected (e.g., similar to a standard delivery truck). This rigid connection decreases the overall footprint of the MRTA 10.

The patient treatment compartment 20 includes at least one patient access door 14 to permit access to and egress from the interior of the patient treatment compartment 20. The patient access door 14 may include ramps or other lifting devices to improve access for non-ambulatory patients. The patient treatment compartment 20 includes a plurality of radiation shielding sections 18a-e (e.g. lead, aluminum, alloys of lead, polymers (such as acrylic), concrete and fiberglass). The position and number of radiation shield sections 18a-e is exemplary only and not a limitation as additional sections of radiation shielding will be included to meet existing shielding requirements (e.g., federal and state regulations, ALARA recommendations). Also, the thickness and location of the radiation shielding sections 18a-e is dependent on the material used and the configuration of the interior of the patient treatment compartment 20 (e.g. the location of the radiation source, the treatment table and interior radiation shields).

The radiation shielding may be in the form of walls that are tapered in thickness according to position from the centerline of a high dose rate radiation source, the position being calculated based upon perpendicular rays transverse to the radiation shielding, whereby a savings in weight is accomplished. The walls may be tapered in height as they approach the high dose rate radiation source.

The whole of the MRTA 10 is considered as a radiation vault with shielding affixed and disposed on the practicable outer boundary of the MRTA 10 (e.g., on the body of the MRTA vehicle, and on a divider behind the driver compartment). For example, as shown in FIG. 1, a MRTA 10 with dimensions of approximately 29 feet in length, by 8 feet in width, with an inner height of 6 feet. With a radiation source located in the center of the MRTA 10, the thickness of the radiation shielding sections at the front and rear of the MRTA 10 (i.e., sections 18b,c) is approximately 1.37 inches of lead. The thickness of the radiation shielding on the sides of the MRTA 10 (i.e., sections 18a,d) is approximately 0.88 inches of lead. The thickness of the radiation shielding on the ceiling of the MRTA 10 (i.e., section 18e) is approximately 1.18 inches of lead. These values are exemplary only as the number, geometry and thickness of the sections will be modified based on the radiation source configuration as well as patient table shielding, and optional interior shielding, if any.

The MRTA 10 is capable of generating and receiving power and communication signals. The interface panel 16 includes connection ports for power and communication systems. For example, the patient treatment compartment 20 is capable of receiving power (e.g. 120 v, 60 Hz) and communication inputs (e.g. cable television signals, Internet access) from external sources. The interface panel 16 is also capable of providing power from generators and batteries installed within the MRTA 10, and communication signals from onboard computer systems, in support of detached operations. The wireless antenna 22 is a component of an onboard computer system and provides access to the Internet via commercial broadband signals (e.g. Verizon BroadbandAccess™). The wireless antenna 22 also supports a wireless local area network (e.g. Wi-Fi, Bluetooth, WIMAX, HomeRF) to support detached operations.

Figure 2:
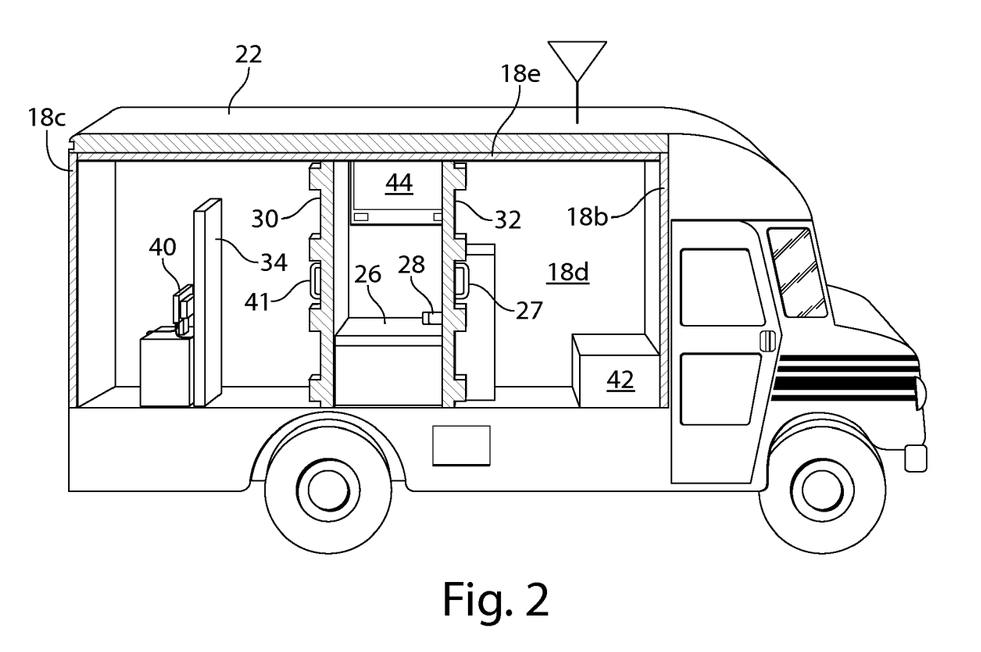
FIG. 2 a partial interior view of a mobile radiation therapy apparatus.

Regarding FIG. 2, the patient treatment compartment 20 includes a treatment table 26, a radiation source 28, optional patient area radiation bulkheads 30, 32 with access doors 27, 41, and operator radiation shielding 34, an operator control station 40, a control power system 42, and a patient entertainment device 44. In general, the patient treatment compartment 20 is configured to include an interior that is conducive to patient relaxation (e.g., soft lighting, frosted glass partitions etched with scenes of local beauty, and a sound system for appropriate music). In one embodiment, the treatment table 26 is enclosed within optional patient area radiation bulkheads 30, 32 (e.g. lead, or titanium for standard radiation protection). The treatment table 26 is also comprised of radiation shielding material. The optional patient area radiation bulkheads 30, 32, and the material within the treatment table 26, are of sufficient density to provide a partial barrier during High Dose Rate (HDR) implant therapy. For example, the optional patient area radiation bulkheads 30, 32 is comprised of 0.46 inches of lead.

The access doors 27, 41 are composed of radiation shielding material (e.g. lead or titanium) and are configured to allow patients and medical personnel to enter the treatment table 26. The doors 27, 41 include, or are capable of integrating with, patient transfer systems to assist in moving a patient from a stretcher, wheelchair, or seat, to the treatment table 26. INSERT BRANDS/TYPES OF TRANSFER SYSTEMS (IF KNOWN). Further, the treatment table 26 is configured to rotate the patient to an appropriate position for therapy.

The radiation source 28 is configured to provide a dosage appropriate for a prescribed therapy plan. In general, the radiation source 28 includes a 192Ir source. For example, if the therapy plan requires a variable low dose rate, then the MRTA 10 will be configured with a Nucletron microSelect PDR™ as the radiation source 28. In another example, if the therapy plan requires a high dose rate, then the MRTA 10 will be configured with a Nucletron microSelect HDR™ as the radiation source 28. The invention is not limited to the selection of a single Nucletron source, nor is it limited to a single supplier of radiation sources. In another example, the Xoft Axxent™ HDR X-ray Source 2.2 and associated Axxent™ controller will be used. Further, in addition to the radiation source 26, the MRTA 10 is configured with an optional portable X-ray imaging device.

The disposition of the radiation source 28 in FIG. 2 is exemplary only and not a limitation as alternative mounting configurations are also envisioned. For example, the radiation source 28 is mounted on the ceiling of the MRTA 10 and disposed to deliver radiation to a patient below. Further, multiple sources are installed in a single MRTA 10 such as from both a side and an overhead mount. Portable radiation sources are also included in the MRTA 10 as bulkhead spares, to be configured prior to a radiation therapy session. Combinations of sources rigidly fixed within the MRTA 10, and portable sources which are stored within the MRTA 10 are envisioned. Further, portable sources will be configured to connect to the interface panel 16 during detached operations.

The operator control station 40 is disposed behind radiation shielding 34 and is operable connected to the MRTA 10. For example, the radiation shielding 34 is approximately 1 inch thick lead, and is disposed to shield an operator working at the control station 40. In one embodiment, the radiation shielding 34 is divided into 2 sections such that the upper section is comprised of 1 inch thick lead, and the lower section is comprised of 0.53 inch thick lead. The reduction in lead for the lower half of the shielding 34 is based on the influence of the optional patient area bulkhead 30 and the patient table 26.

The operator control station 40 comprises networked computer processors, the computer processors including input and output devices, and configured to control the MRTA 10 sub-systems (e.g. doors and interlocks, patient table height and orientation, climate control, power generation, Internet connectivity) as well as control the radiation source and store patient therapy data. The power control system 42 includes power generation and control equipment capable of providing electrical power to the MRTA 10, including the radiation source 22 and operator control station 40. In one embodiment, the power control system 42 receives electrical power through the interface panel 16 thus reducing the need to generate power within the MRTA 10.

The patient entertainment device 44 is disposed within sight of the patient table 26 and is configured to provide multimedia content to the patient during therapy.

Figure 3:
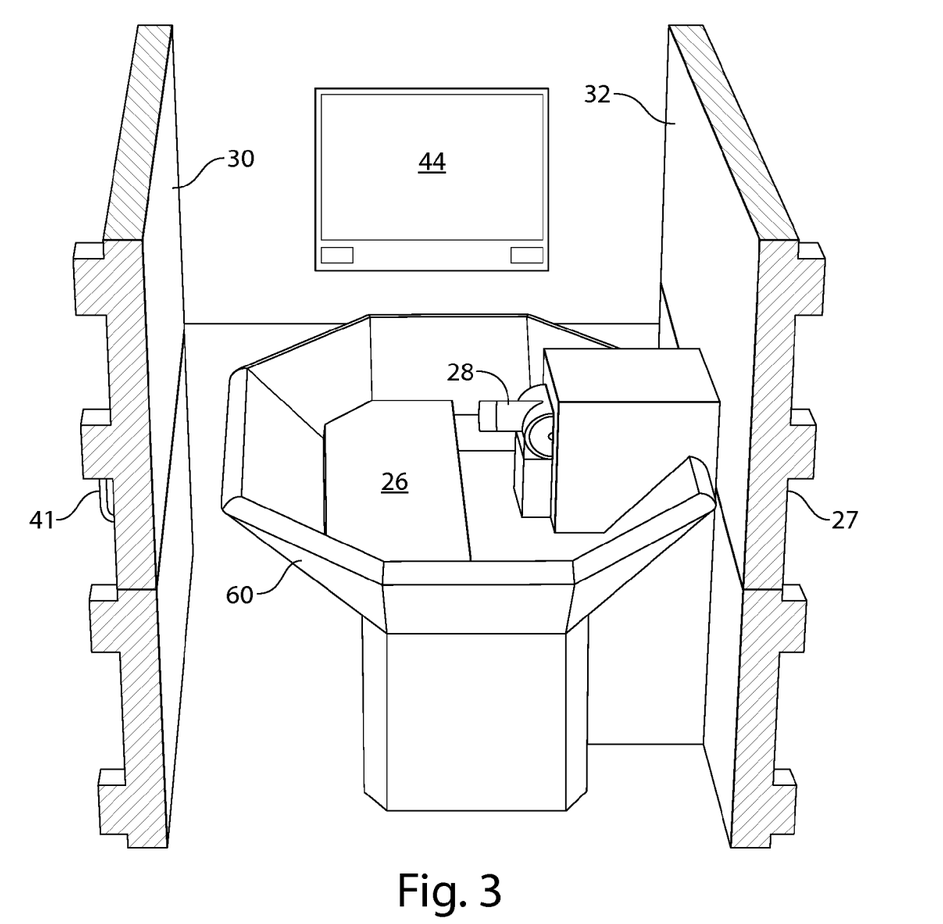
FIG. 3 a view of an octagon patient table shield with optional patient area shielding.

Regarding FIG. 3, with further reference to FIG. 2, the patient treatment compartment 20 in the MRTA 10 includes the treatment table 26, the radiation source 28, optional patient area radiation bulkheads 30, 32 with access doors 27, 41, a patient entertainment device 44, and an octagon patient table shield 60. The octagon patient table shield 60 is configured around the patient table 26 and disposed to reduce the amount radiation energy entering the patient treatment compartment 20. The height and configuration of the octagon patient table shield 60 is exemplary only, as the location of type of radiation source will impact the necessary geometry of the radiation shielding. As known in the art, post installation adjustments of the radiation shielding (e.g., 18*a-e*, 30, 32, 34, and 60) will be required to reduce hot spots within and beyond the MRTA 10.

Figure 4:
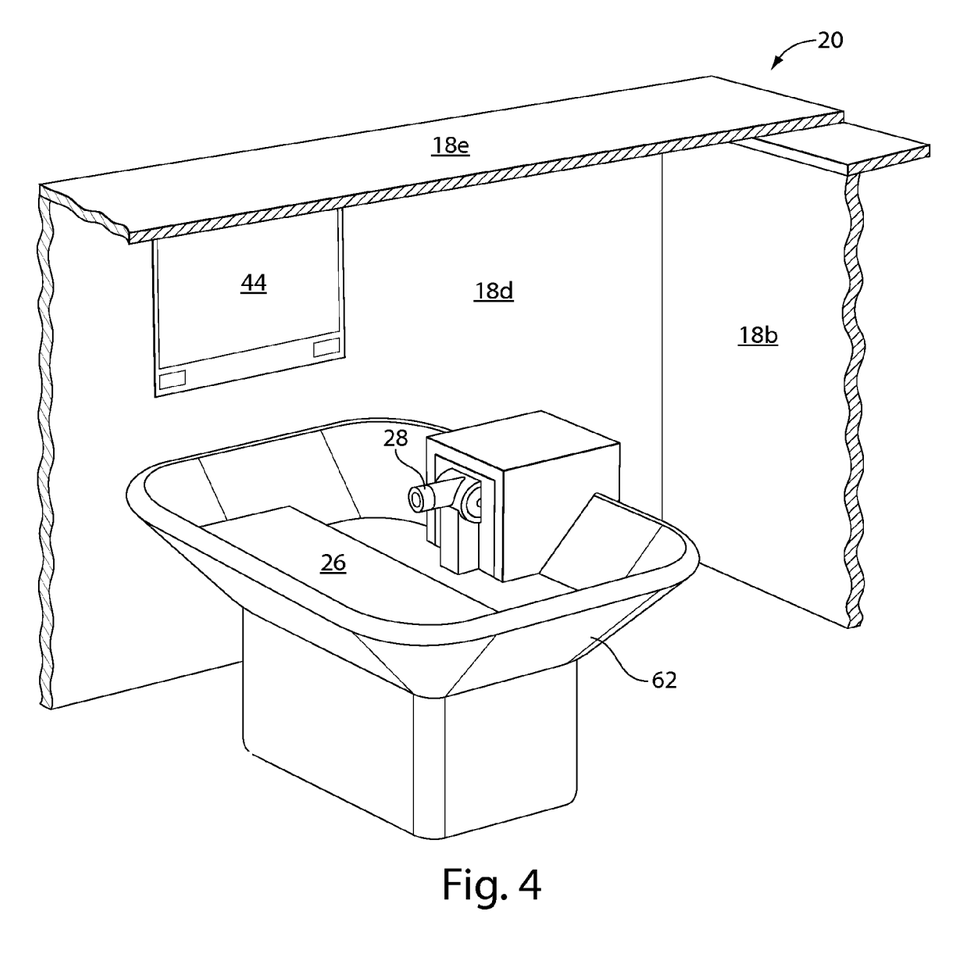
FIG. 4 a view of an oval shaped patient table shield.

Referring to FIG. 4, with further reference to FIGS. 1-3, the patient treatment compartment 20 includes a treatment table 26, the radiation source 28, the patient entertainment device 44, and an oval patient table shield 62. The patient treatment compartment 20 is enclosed by radiation shield sections 18*a-e* (n.b., radiation shield sections 18*a,c* are not shown in FIG. 4 because of the perspective of the illustration). The height and angle of the oval patient table shield 62 are exemplary, and not a limitation as the configuration will change based on the relative location of the radiation source 28. In one embodiment, portions of the patient table shield 62 are on hinges and configured to fold down to provide direct access to the treatment table 26. The hinged portion of the patient table 62 is further configured to lock in the upright position after a patient is placed on the treatment table 26.

Figure 5:
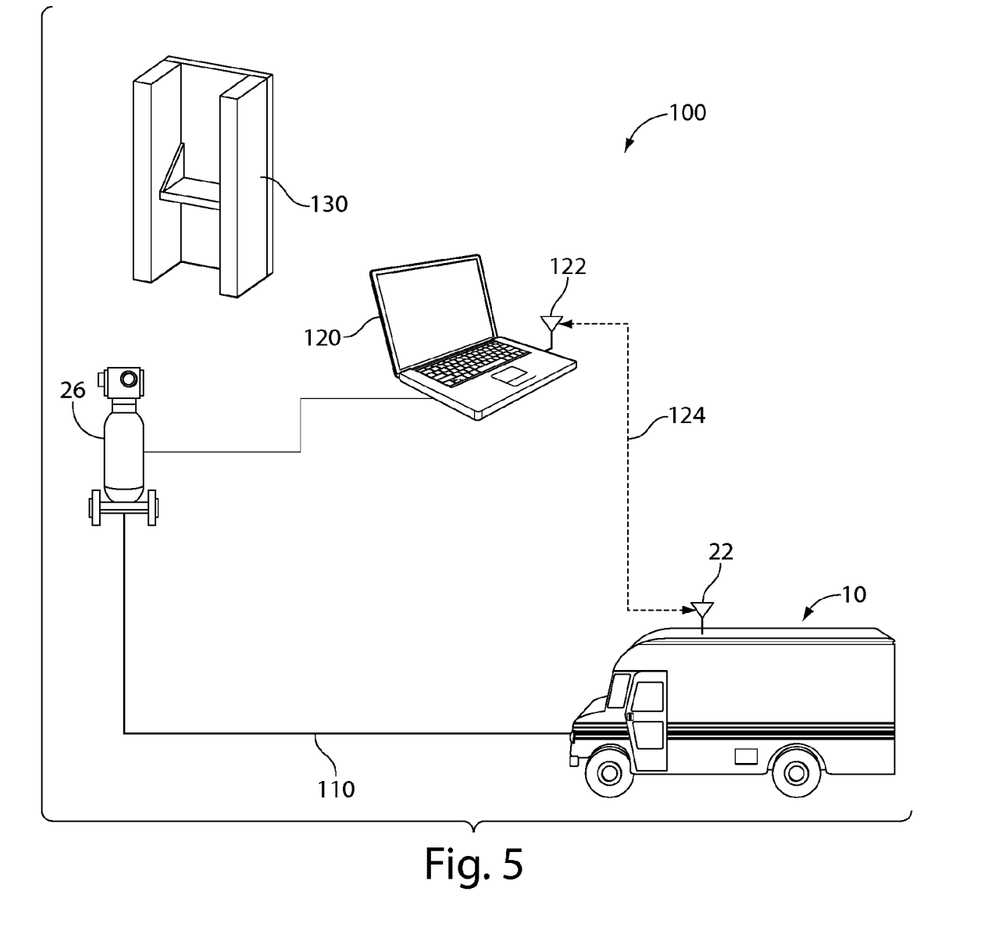
FIG. 5 a system diagram of detached radiation therapy configuration.

Referring to FIG. 5, with further reference to FIG. 1, a system diagram of detached radiation therapy 100 is shown. Detached operation includes the MRTA 10, the communication antenna 22, the radiation source 26, a control tether 110, a local computer 120, a wireless network interface 122, a wireless data connection 124, and portable shielding 130. The MRTA 10 is configured to connect to the control tether 110 through the interface port 16. The control tether 100 includes power and data communication portions, and is configured to connect to the radiation source 26. The local computer 120 connects to the radiation source 26 and is configured with corresponding control software for monitoring and controlling the radiation source 26. The local computer 120 is also configured to communicate with the MRTA 10 through the control tether 100, or via wireless network interface 122, and the wireless data connection 124. The portable shielding 130 is configured to be removed from the MRTA 10 and moved into a residential space (e.g., through standard doors and stairwells). The portable shielding 130 is exemplary and not limiting as other configurations of transportable shielding are envisioned.

In operation, the elements within the MRTA 10 such as the radiation source 16, computer control system 40, and bulkheads 30, 32 can be detached from the MRTA 10 and set-up in the patient's home. In detached operation 100, the elements of the MRTA are tethered to the MRTA 10 via a control tether 110, including cables for power and data communications. The data communication between the local computer 120 and the MRTA 10 is established via wireless link 122, 124, 22. The computer control system 40 is capable of bridging the wireless link 122, 124, 22 to the internet. In one embodiment, power to the radiation source 26 is provided locally from the patient's residential service. Also, the portable radiation shielding 130 is configured to collapse to 2.5×2.5 feet and expand up to 5×7 feet.

Figure 6:
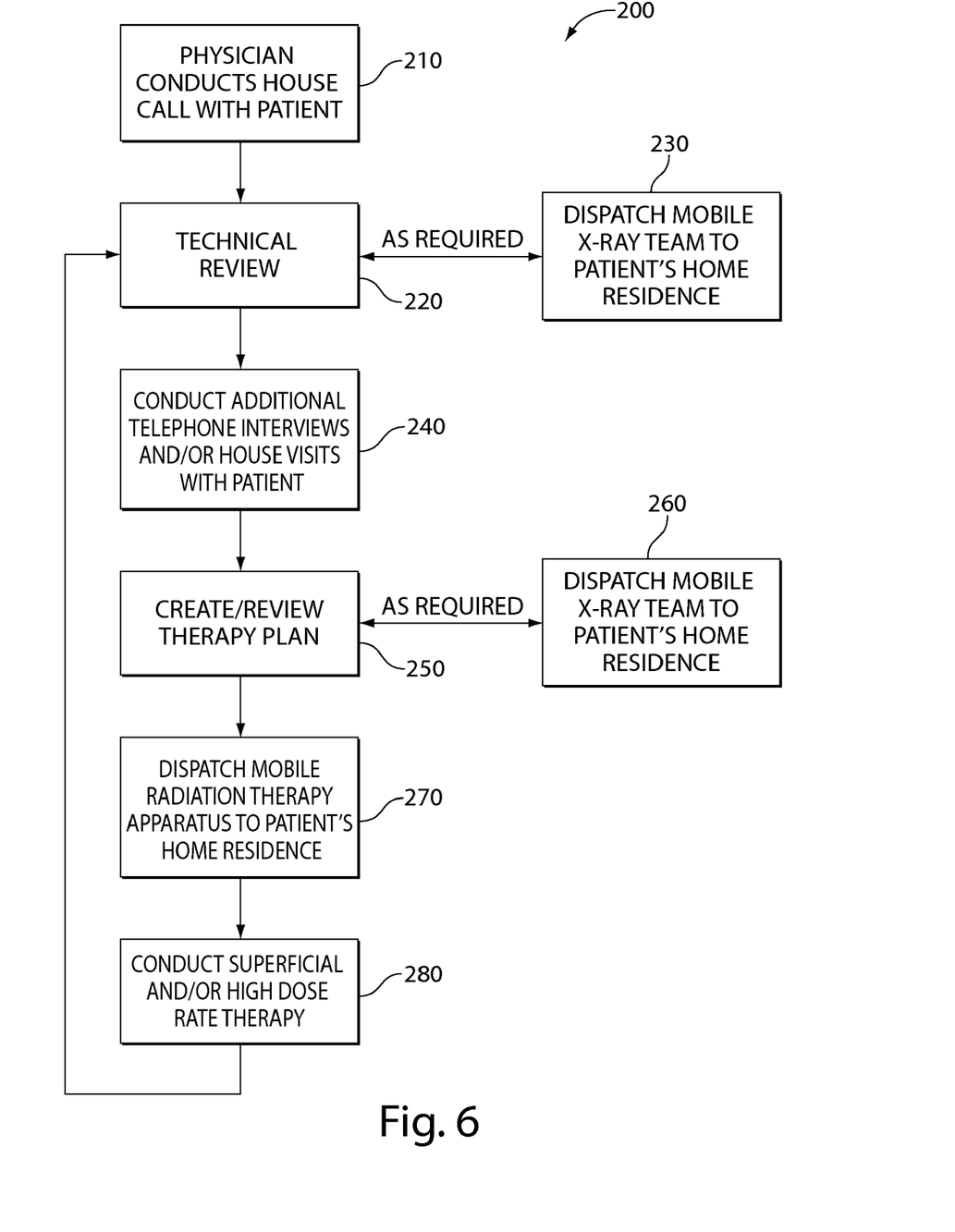
FIG. 6 a process flow chart for providing mobile radiation therapy.

In operation, referring to FIG. 6, with further reference to FIGS. 2-5, a process 200 for providing mobile radiation therapy using the MRTA 10 includes the stages shown. The process 200, however, is exemplary only and not limiting. The process 200 may be altered, e.g., by having stages added, removed, or rearranged.

At stage 210, a physician makes a house call in order to assess a patient. The house call includes general patient consulting, actual physical tumor measurements, assessments of normal adjacent dose limiting structures, treatment planning, and obtaining digital photos, as well as portable x-rays where necessary. Also, all consent forms are obtained at the initial consult, including HIPPA forms and any other forms and insurance information. This initial house call can be more than just information gathering. For example, it creates a personal bond between the patient and physician and helps increase patient commitment to the program and thereby increase chances for successful treatment.

At stage 220, the physician takes the information back to a centralized headquarters area for technical review. A technical review involves a technical department (e.g. therapists, dosimetrists, nurses, and physicists), or similar staff to complete a technical analysis. The technical department processes the information as needed to plan a therapy. For example, additional x-rays may be required, in which case a MRTA 10 will be dispatched to obtain them at stage 230. The technical department also accesses existing x-rays available via hard films (CT scans, PET scans, MRI scans, Bone scans, etc.), or via digital mediums such as memory discs or the internet.

At stage 240, and based on the technical review at stage 220, additional telephone phone contact with the patient, as well as additional visits may be required. This individual treatment helps to ensure that the patient feels a sense of individual commitment as well as confidence in the treatment program. This sense of commitment in turn helps improve compliance with the prescribed therapy. The individual treatment also helps reduce the frustrations associated with stationary cancer centers, such as the long queue time patients must endure while simultaneously being surrounded by sick patients who are often likely complain and promote a pessimistic outlook.

At stage 250, a radiation therapy plan is created or reviewed by the physician. Additional x-rays will be obtained by dispatching a MRTA 10 to the patient's home residence at stage 260.

At stage 270, the MRTA 10 is dispatched to the patient's home residence or other appropriate location. A simulation is performed on site (i.e., the patient's home residence) by the physician in the mobile radiation therapy unit. The dispatched MRTA 10 is equipped with the appropriate radiation source 28 to complete the therapy plan indicate at stage 250 (e.g., low dose rate and high dose rate sources). The MRTA 10 vehicle is sufficiently compact in size to travel to the patient's residence to begin therapy in the patient's parking lot or residential driveway (e.g. the MRTA 10 compartment is approximately 28' long by 8' wide).

At stage 280, the patient under goes radiation treatment in accordance with the prescribed therapy plan as indicated at stage 250.

Embodiments of the MRTA 10 include pop-out walls located on the side of the vehicle. The pop-out walls are configured to decreased radiation leakage. Also a sliding lead lined panel with treatment viewing window may cover the pop out to create a place for the technician and physicist to stand during treatment Also, a possible shielded drape over or on top of the applicator may allow decreased shielding requirements in the walls. The MRTA 10 is also configured with interlocks to secure the radiation source 28 when a potentially unsafe condition exists (e.g., open doors, vehicle movement, high radiation sensors).

Another embodiment includes an MRTA 10 configured to provide chemotherapy including exam tables, seats, and intravenous apparatus along with standard monitoring equipment and personnel required during chemotherapy. Other embodiments of the MRTA 10 is configured to allow mobile surgery simultaneously with intra-operative radiation therapy, or post-operative radiation therapy and chemotherapy in a mobile setting.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

While the invention has been particularly shown and described with reference to a preferred embodiment thereof, it will be understood by those skilled in the art that various changes in form and details may be made therein without departing from the spirit and scope of the invention.

The embodiments of the invention in which an exclusive property or privilege is claimed are defined as follows:

1. A mobile radiation treatment apparatus comprising:
   a radiation source configured to emit radiation;
   a patient treatment table disposed in proximity to the radiation source;
   an operator control station;
   an operator shield assembly disposed between the operator control station and the radiation source, the operator shield assembly configured to reduce exposure to a user located at the operator control station from the radiation emitted from the radiation source;
   a plurality of shielding sections configured to enclose the radiation source, the patient treatment table, the operator control station, and the operator shield assembly in a compartment, wherein the compartment is at most approximately 29 feet in length, 9 feet in width, and 8 feet in height, and the plurality of shielding sections are disposed to substantially impede the radiation emitted from the radiation source, further comprising a patient table shield disposed around the patient treatment table, and configured to impede the radiation emitted from the radiation source.

2. The mobile radiation treatment apparatus of claim 1, wherein the shape of patient table shield is substantially similar to an octagon.

3. The mobile radiation treatment apparatus of claim 1, wherein the shape of patient table shield is substantially similar to an oval.

4. The mobile radiation treatment apparatus of claim 1, wherein a portion of the patient table shield is pivotably connected to the patient treatment table such that the portion of the patient table shield can be lowered to allow direct access to the patient treatment table.

5. A mobile radiation therapy apparatus comprising:
   a vehicle cabin including driving controls for the vehicle;
   vehicle cabin equipped with an infra red heat sensor device, motion detector and metal bar across seats to prevent any breach of security all triggering automatic shut off;
   a patient treatment compartment rigidly attached to the vehicle cabin;
   a radiation source configured to emit radiation, and disposed within the patient treatment compartment;
   a patient treatment table disposed within the patient treatment compartment and in proximity to the radiation source;
   a treatment table radiation shield disposed around the patient treatment table, and configured to impede the radiation emitted from the radiation source;
   a plurality of radiation shield sections rigidly attached to the patient treatment compartment, and configured to substantially impede the radiation emitted from the radiation source.

6. A mobile radiation therapy apparatus comprising:
   a vehicle cabin including driving controls for the vehicle cabin;
   a patient treatment compartment rigidly attached to the vehicle cabin;
   a high dose rate radiation source configured to emit radiation, and disposed within the patient treatment compartment;
   a multisided patient treatment table disposed within the patient treatment compartment and in proximity to the radiation source;
   a radiation shield disposed around the patient treatment table, said radiation shield including a plurality of radiation shield sections rigidly attached to the patient treatment compartment, and configured to substantially impede the radiation emitted from the radiation source.

7. The mobile radiation therapy apparatus of claim 6, wherein said patient treatment table comprises flanges extending upward to capture radiation from said high dose rate radiation source.

8. The mobile radiation therapy apparatus of claim 6, wherein said patient treatment table is octagonal.

9. The mobile radiation therapy apparatus of claim 6, further comprising pop outs on sides of the apparatus to secure the perimeter from pedestrians and pets.

10. The mobile radiation therapy apparatus of claim 9, wherein said pop outs are configured to be waiting areas for technicians and physicists, and comprise a covering panel and viewing window with a view of a treatment area.

11. The mobile radiation therapy apparatus of claim 6, further comprising a patient treatment area radiation shielding in the form of walls that are tapered in thickness according to position from the centerline of said high dose rate radiation source, said position being calculated based upon perpendicular rays transverse to said patient treatment area radiation shielding, whereby a savings in weight is accomplished.

12. The mobile radiation therapy apparatus of claim 6, further comprising radiation shielding walls which are tapered in height as they approach the high dose rate radiation source.

13. The mobile radiation therapy apparatus of claim 6, wherein the apparatus is further configured for non-high-dose-rate therapy.

14. The mobile radiation therapy apparatus of claim 13, wherein said non-high-dose-rate therapy comprises a therapy selected from the set consisting of: low dose particle therapy, ytterbium 169, protons, neutrons, low frequency vacuum tube, cyber knife, or XRT therapy.

15. The mobile radiation therapy apparatus of claim 5, wherein the radiation source is configured to emit radiation for high-dose radiation therapy.

16. The mobile radiation therapy apparatus of claim 5, wherein the radiation source is configured to emit radiation to support variable low dose rate therapy.

17. The mobile radiation therapy apparatus of claim 15, further comprising:
   a control tether for connecting the patient treatment compartment to the radiation source, wherein the radiation source is relocated outside of the patient treatment compartment;
   a plurality of portable radiation shields configured to be removed from the patient treatment compartment and disposed in proximity to the radiation source; and,
   a control computer operation center operably connected to the radiation source and configured to control the radiation emitted by the radiation source.

18. The mobile radiation therapy apparatus of claim 5, further comprising a wireless connection to the internet.

19. The mobile radiation therapy apparatus of claim 5, further comprising an x-ray imaging system.

20. The mobile radiation therapy apparatus of claim 5, further comprising a chemotherapy treatment device, wherein the patient treatment compartment is utilized to provide chemotherapy to a patient.

* * * * *